United States Patent
Nifant'ev et al.

(10) Patent No.: US 6,271,411 B1
(45) Date of Patent: Aug. 7, 2001

(54) PROCESS FOR PREPARING 2-ARYL-SUBSTITUTED INDENES

(75) Inventors: Ilya E. Nifant'ev, Moscow (RU); Yuri A. Dubitsky, Milan (IT); Alexander A. Sitnikov, Moscow (RU)

(73) Assignee: Montell Technology Company bv (NL)

( * ) Notice: Subject to any disclaimer, the term of this patent is extended or adjusted under 35 U.S.C. 154(b) by 0 days.

(21) Appl. No.: 09/202,319

(22) PCT Filed: Apr. 9, 1998

(86) PCT No.: PCT/EP98/02150

§ 371 Date: Dec. 11, 1998

§ 102(e) Date: Dec. 11, 1998

(87) PCT Pub. No.: WO98/46547

PCT Pub. Date: Oct. 22, 1998

(30) Foreign Application Priority Data

Apr. 15, 1997 (EP) .................................................. 97201112

(51) Int. Cl.[7] ............................. C07L 69/76; C07L 35/08
(52) U.S. Cl. .......................... 560/102; 562/462; 564/428; 568/327; 568/440; 568/652; 568/929; 568/930
(58) Field of Search ........................... 560/102; 562/492; 564/428; 568/929, 930, 327, 440, 632

(56) References Cited

FOREIGN PATENT DOCUMENTS

| 0752428 | 1/1997 | (EP) . |
|---|---|---|
| 0 752 428 | * 1/1997 | (EP) . |
| 6-234973 | * 8/1994 | (JP) . |
| 9620225 | 7/1996 | (WO) . |

OTHER PUBLICATIONS

L. G. Greifenstein et al, J. of Organic Chemistry vol. 46 No. 25, 1981, pp. 5125–5132.*
T. Wolf et al, J. Org. Chemistry vol. 57 No. 15, 1992, pp. 4255–4262.*
Li, S et al Holzforschung vol. 50 No. 3, 1996, pp. 253–257.*
Derwent Abstract of JP 06234973 Aug. 23, 1994.

* cited by examiner

Primary Examiner—Paul J. Killos
(74) Attorney, Agent, or Firm—Bryan Cave LLP

(57) ABSTRACT

A process is disclosed for preparing 2-aryl-substituted indenes by reacting an indene with an arene compound substituted with an halogen atom, preferably a iodine atom, or with an organosulphonate group, said reaction being carried out in a basic medium in the presence of a palladium catalyst. The compounds obtainable by this process can be used to prepare metallocene compounds with transition metals such as titanium, zirconium or hafnium, which are useful as catalyst components in the polymerization of olefins.

16 Claims, No Drawings

PROCESS FOR PREPARING 2-ARYL-SUBSTITUTED INDENES

The present invention relates to a novel process for preparing 2-aryl-substituted indenes, which are useful in the synthesis of metallocene compounds used in olefin polymerization. It is known that the use of metallocene compounds in propylene polymerization gives rise either to amorphous or to crystalline polymers depending on the metallocene used. In particular chiral, bridged metallocene compounds give rise to stereospecific catalysts able to polymerize propylene to highly crystalline polymers. EP-A-185,918 for instance discloses a process for the preparation of isotactic polypropylene in the presence of ethylene-bis (4,5,6,7-tetrahydroindenyl)zirconium dichloride.

WO 95/25757 discloses a catalyst based on unbridged 2-aryl-substituted bis-indenyl metallocenes that permits to obtain partially crystalline thermoplastic-elastomeric stereoblock olefin polymers. The 2-aryl-indene ligands of said metallocenes are prepared by means of a Grignard reaction between 2-indanone and phenylmagnesium bromide and following elimination in acidic environment. Thus, 2-phenyl-1H-indene was prepared according to the following scheme:

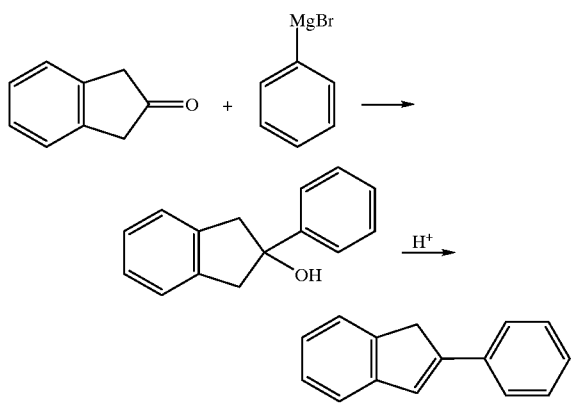

with an overall yield of the two-step reaction of about 65%.

An improvement of the above preparation is disclosed in WO 96/20225. By carrying out the reaction between 2-indanone and phenylmagnesium bromide in the presence of a compound of a metal selected from lanthanum and those of the lanthanide series, particularly cerium chloride, 2-phenyl-1H-indene was obtained with an overall yield of the two-step reaction of about 75%.

However, both of the above mentioned PCT applications disclose the preparation of 2-aryl-indenes wherein the indenes have no other substituents in addition to the aryl group in 2-position. A reason therefore is that substituted 2-indanones are difficult to find commercially and are also difficult to prepare. In fact, the starting 2-indanone is obtained by a reaction of indene with formic peracid according to the following scheme:

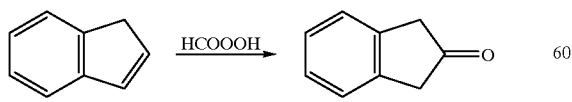

This reaction is very dangerous and the yield is very low (about 40%).

Another limitation of the above preparation process is that it cannot be used to prepare 2-aryl-substituted indenes in which the aryl group has substituents which are not compatible with the Grignard reaction such as, for example, carboxyl or carbonyl groups.

There is therefore the need for a more practical process for the preparation of 2-arylindene compounds allowing to obtain these compounds in high yields and furthermore allowing the preparation of compounds whose synthesis was not possible according to the methods of the prior art.

Chem. Rev., 1989, 89, 1433–1445 describes the Heck coupling reaction of haloarenes with alkenes catalyzed by palladium(0). A proposed mechanism for the coupling of iodobenzene with styrene is the following:

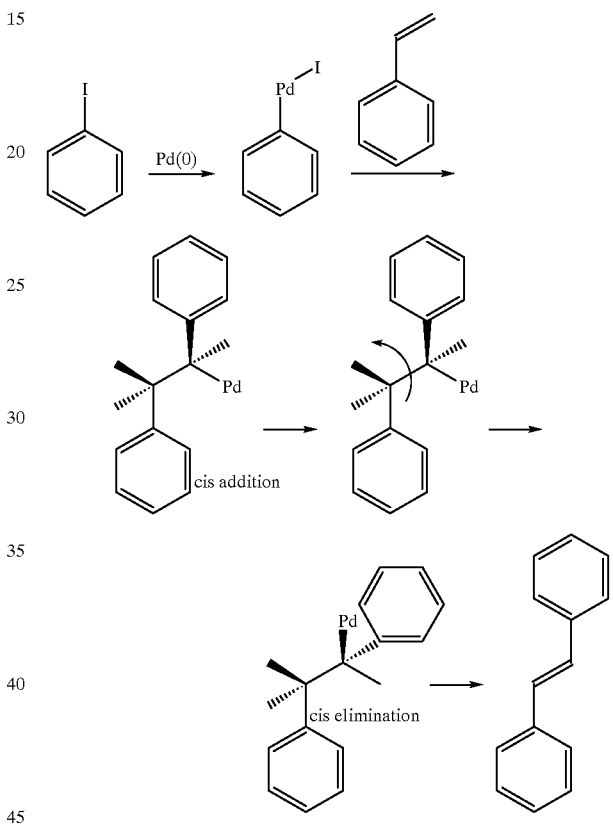

According to this scheme, the reaction has to pass through the steps of cis-addition and cis-elimination. Thus, this reaction would not have been deemed allowed on substrates such as indene because the intermediate deriving from cis-addition to the double bond, i.e.:

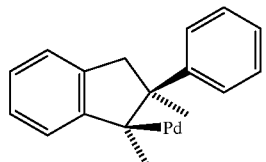

does not allow cis-elimination.

It has now unexpectedly been found that, by operating under particular conditions, it is possible to prepare 2-aryl-substituted indenes and 2-aryl-substituted, bridged bis-indenyls by reacting an indene with an arene compound having, a suitable leaving group.

Thus, according to a first aspect, the present invention provides a process for the preparation of 2-aryl-substituted indenes of the formula (I):

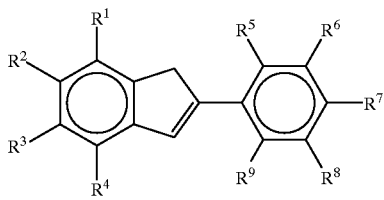

(I)

wherein:

$R^1$, $R^2$, $R^3$, $R^4$, $R^5$, $R^6$, $R^7$, $R^8$ and $R^9$, same or different, are hydrogen atoms, halogen atoms, $C_1$–$C_{20}$ alkyl, $C_3$–$C_{20}$ cycloalkyl, $C_2$–$C_{20}$ alkenyl, $C_6$–$C_{20}$ aryl, $C_7$–$C_{20}$ alkylaryl, $C_7$–$C_{20}$ arylalkyl, $NO_2$, $NR^{10}{}_2$, OH, $OR^{11}$, COOH, $COOR^{12}$, COH or $COR^{13}$ groups, optionally containing Si or Ge atoms, any two adjacent $R^1$, $R^2$, $R^3$, $R^4$, $R^5$, $R^6$, $R^7$, $R^8$ and $R^9$ substituents optionally forming an aromatic or aliphatic ring comprising from 5 to 8 carbon atoms, and one of $R^1$, $R^2$, $R^3$, $R^4$, $R^5$, $R^6$, $R^7$, $R^8$ and $R^9$ being optionally linked with a corresponding $R^1$, $R^2$, $R^3$, $R^4$, $R^5$, $R^6$, $R^7$, $R^8$ and $R^9$ of a second compound of the formula (I) to form a structural bridging group; $R^{10}$, $R^{11}$, $R^{12}$ and $R^{13}$ being $C_1$–$C_{20}$ alkyl, $C_3$–$C_{20}$ cycloalkyl, $C_2$–$C_{20}$ alkenyl, $C_6$–$C_{20}$ aryl, $C_7$–$C_{20}$ alkylaryl or $C_7$–$C_{20}$ arylalkyl radicals; optionally an aromatic carbon atom of the indene ring being replaced by a hetero atom selected from those belonging to group 15 of the Periodic Table of the Elements (new IUPAC version). the $R^1$, $R^2$, $R^3$ or $R^4$ substituent on the replaced carbon atom being absent, said process comprising the reaction of an indene of the formula (H):

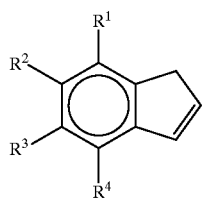

(II)

wherein $R^1$, $R^2$, $R^3$ and $R^4$ have the meaning given above, one of $R^1$, $R^2$, $R^3$ and $R^4$ being optionally linked with a corresponding $R^1$, $R^2$, $R^3$ and $R^4$ of a second indene of the formula (II) to form a structural bridging group, optionally an aromatic carbon atom of the indene ring being replaced by a hetero atom selected from those belonging to group 15 of the Periodic Table of the Elements (new IUPAC version), the $R^1$, $R^2$, $R^3$ or $R^4$ substituent on the replaced carbon atom being absent; with an arene compound of the formula (E):

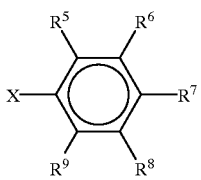

(III)

wherein X is an halogen atom, preferably a iodine atom, or an organosulphonate group, $R^5$, $R^6$, $R^7$, $R^8$ and $R^9$ have the meaning given above, one of $R^5$, $R^6$, $R^7$, $R^8$ and $R^9$ being optionally linked with a corresponding $R^5$, $R^6$, $R^7$, $R^8$ and $R^9$ of a second arene compound of the formula (III) to form a structural bridging group; said reaction being carried out in a basic medium in the presence of a palladium catalyst.

The reaction of the invention has to be carried out in a basic medium. Suitable bases for use in the process of the present invention include:

primary, secondary or tertiary amines, such as thriethylamine;

alkali or earth-alkali metal hydroxides, such as lithium hydroxide, sodium hydroxide, potassium hydroxide, calcium hydroxide, barium hydroxide;

alkali or earth-alkali metal carbonates or hydrocarbonates, such as sodium carbonate, potassium carbonate;

alkali or earth-alkali metal alcoholates, such as sodium ethylate, potassium tern-butylate;

quaternary ammonium hydroxides or alkoxides, such as tetrabutylammonium hydroxide tetrabutylammonium ethoxide.

The reaction of the invention can suitably by carried out in any solvent commonly used in this kind of reaction, such as dimethyl sulphoxide (DMSO), N,N-dimethylformamide (DMF), sulpholane, N-methylpyrrolidone, N,N-dimethylacetamide, tetrahydrofurane (THF), ethers, hexamethylphosphoramide.

According to a preferred embodiment, the reaction of the invention is carried out in the presence of a base which acts as a solvent. Bases suitable for this purpose are the tertiary amines such as the triethyl amine.

According to a more preferred embodiment, the reaction of the invention is carried out in a mixture containing a polar solvent and a tertiary amin.

According to a most preferred embodiment, the reaction of the invention is carried out in a mixture containing N,N-dimethylformamide (DMF) and triethyl amine.

In the reaction of the invention the volume ratio of the polar solvent to the tertiary amin can vary in a very wide range. Generally, the volume ratio of the polar solvent to the tertiary amin is in the range from 1:100 to 100:1. Thus, according to the preferred embodiments of the invention the content of the polar solvent can be varied from 1% to 99% by volume. By operating in a mixture containing in addition to the tertiary amine a polar solvent such as DMF a higher yield of the desired product can be obtained.

Palladium catalysts suitable for use in the reaction of the invention are palladium(0) and palladium(II) compounds such as, for example, the palladium (II) salts of mono- or dicarbossilic acids. A preferred palladium compound is palladium acetate.

In the arene compound of the formula (III), X is an halogen atom, preferably a iodine atom, or an organosulphonate group, such as a tosylate or mesylate group. The $R^5$ and $R^9$ substituents are preferably hydrogen atoms.

Preferably, in the reaction of the invention the indene of the formula (II) and the arene compound of the formula (III) are used in substantially equimolar amounts.

The temperature of the reaction of the indene of the formula (II) with the arene compound of the formula (III) is not critical. It can typically range from about 0° C. to 160° C. and, preferably, from about 60° C. to 120° C. The reaction can suitably be carried out under reflux of the solvent. Examples of 2-aryl-substituted indenes obtainable with the process of the present invention are:

2-phenyl-indene;

2-(4-methyl-phenyl)-indene;

2-(4-t-butyl-phenyl)-indene;
2-(4-phenyl-phenyl)-indene:
2-(4-fluoro-phenyl)-indene;
2-(4-chloro-phenyl)-indene;
2-(4-nitro-phenyl)-indene;
2-(4-methoxy-phenyl)-indene;
2-(4-carbethoxy-phenyl)-indene;
2-(4-carboxy-phenyl)-indene;
2-(4-trfluoromethyl-phenyl)-indene;
2-(3,5-dimethyl-phenyl)-indene;
2-(3,5-bis-trifluoromethyl-phenyl)-indene;
2-phenyl-4,7-dimethyl-indene;
2-phenyl4,6-dimethyl-indene;
2-phenyl-5,6-dimethyl-indene;
2-phenyl4,5,6,7-tetramethyl-indene;
2-phenyl-benzindenes;
2-(4-methoxy-phenyl)-benzindenes;
2-(4-carbethoxy-phenyl)-benzindenes:
2-(1-naphtyl)-indene;
4,4'-bis-(2-indenyl)-1,2-diphenylethane;
1,2-bis(2-phenyl-4-indenyl)ethane
2-phenyl-4-aza-indene;
2,5-diphenyl-4-aza-indene;
2-(4-methyl-phenyl)4-aza-indene;
2-(4-t-butyl-phenyl)-4-aza-indene;
2-(4-phenyl-phenyl)-4-aza-indene;
2-(4-fluoro-phenyl)4-aza-indene;
2-(4-chloro-phenyl)-4-aza-indene;
2-(4-nitro-phenyl)-4-aza-indene;
2-(4-methoxy-phenyl)-4-aza-indene;
2-(4-arbethoxy-phenyl)-4-aza-indene;
2-(4-carboxy-phenyl)-4-aza-indene;
2-(4-trifluoromethyl-phenyl)-4-aza-indene;
2-(3,5-dimethyl-phenyl)-4aza-indene;
2-(3,5-bis-trifluoromethyl-phenyl)-4-aza-indene;
2-phenyl-5,6-dimethyl-4aza-indene;
2-phenyl-benz-4-aza-indenes;
2-(4-methoxy-phenyl)-benz-4-aza-indenes;
2-(4-carbethoxy-phenyl)-benz-4-aza-indenes;
2-(1-naphtyl)-4-aza-indene;
4,4'-bis-(4-aza-2-indenyl)-1,2-diphenylethane.

The 2-aryl-substituted indenes obtained from the reaction of the indene of the formula (II) with the arene compound of the formula (III) according to the present invention can be recovered and separated from the reaction mixture by known techniques such as extraction, crystallization, distillation, chromatography etc.

The 2-aryl-substituted indenes obtainable by the process of the present invention can be employed to prepare the corresponding metallocene compounds with transition metals such as titanium, zirconium of hafnium, which are useful as catalytic components in the polymerization of olefins.

Not only the process of the present invention allows to improve the economy of the preparation of the known 2-aryl-substituted indenes, but it also permits to make available those compounds which the processes of the prior art were not able to prepare.

Therefore, according to another aspect, the present invention provides a 2-aryl-substituted indene of the formula (I):

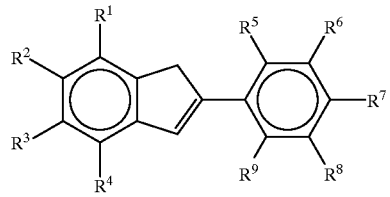

(I)

wherein $R^1$, $R^2$, $R^3$, $R^4$, $R^5$, $R^6$, $R^7$, $R^8$ and $R^9$, same or different, have the meaning given above, with the proviso that at least one of $R^1$, $R^2$, $R^3$, $R^4$, $R^5$, $R^6$, $R^7$, $R^8$ and $R^9$, preferably one of $R^6$, $R^7$ and $R^8$, more preferably $R^7$, is a $NO_2$, $NR^{10}{}_2$, OH, $OR^{11}$, COOH, $COOR^{12}$, COH or $COR^{13}$ group, $R^{10}$, $R^{11}$, $R^{12}$ and $R^{13}$ being $C_1$–$C_{20}$ alkyl, $C_3$–$C_{20}$ cycloalkyl, $C_2$–$C_{20}$ alkenyl, $C_6$–$C_{20}$ aryl, $C_7$–$C_{20}$ alkylaryl or $C_7$–$C_{20}$ arylalkyl groups.

Examples of the above new 2-aryl-substituted indenes are:

2-(4-nitro-phenyl)-indene;
2-(4-methoxy-phenyl)-indene;
2-(4-carbethoxy-phenyl)-indene;
2-(4-carboxy-phenyl)-indene;
2-(4-methoxy-phenyl)-benzindenes;
2-(4-carbethoxy-phenyl)-benzindenes;

According to a further aspect, the present invention provides a 2-aryl-substituted indene of the formula (I):

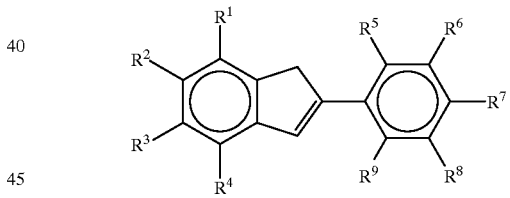

(I)

wherein $R^1$, $R^2$, $R^3$, $R^4$, $R^5$, $R^6$, $R^7$, $R^8$ and $R^9$, same or different, have the meaning given above, one of $R^1$, $R^2$, $R^3$, $R^4$, $R^5$, $R^6$, $R^7$, $R^8$ and $R^9$ and the corresponding $R^1$, $R^2$, $R^3$, $R^4$, $R^5$, $R^6$, $R^7$, $R^8$ and $R^9$ of a second compound of the formula (I) being replaced by a structural bridging group linking the two indenes.

The structural bridging group is preferably an alkylene group.

Non-limiting examples of the above new 2-aryl-substituted indenes are:

4,4'-bis-(2-indenyl)-1,2-diphenylethane;
1,2-bis(2-phenyl-4-indenyl)ethane.

According to a still further aspect, the present invention provides a 2-aryl-substituted indene of the formula (I):

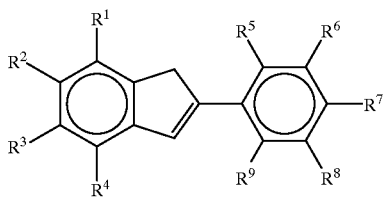

(I)

wherein R¹, R², R³, R⁴, R⁵, R⁶, R⁷, R⁸ and R⁹, same or different, have the meaning given above, wherein an aromatic carbon atom of the indene ring is replaced by a hetero atom selected from those belonging to group 15 of the Periodic Table of the Elements (new IUPAC version), the R¹, R², R³ or R⁴ substituent on the replaced carbon atom being absent.

Non-limiting examples of the above new 2-aryl-substituted indenes are:

2,5-diphenyl-4-aza-indene;
2-phenyl-4-aza-indene;
2-(4-methyl-phenyl)-4-aza-indene;
2-(4-t-butyl-phenyl)-4-aza-indene;
2-(4-phenyl-phenyl)-4aza-indene;
2-(4-fluoro-phenyl)-4-aza-indene;
2-(4-chloro-phenyl)-4-aza-indene;
2-(4-nitro-phenyl)-4-aza-indene;
2-(4-methoxy-phenyl)-4aza-indene;
2-(4-carbethoxy-phenyl)-4-aza-indene;
2-(4-carboxy-phenyl)-aza-indene;
2-(4-trifluoromethyl-phenyl )-4-aza-indene;
2-(3,5-dimethyl-phenyl)-4-aza-indene;
2-(3,5-bis-trifluoromethyl-phenyl)-4-aza-indene;
2-phenyl-5,6-dimethyl-4-aza-indene;
2-phenyl-benz-4-aza-indenes;
2-(4-methoxy-phenyl)-benz-4-aza-indenes;
2-(4-carbethoxy-phenyl)-benz-4-aza-indenes;
2-(1-naphtyl)-4-aza-indene;
4,4'-bis-(4-aza-2-indenyl)-1,2-diphenylethane.

Further advantages of the present invention are made clear by the following examples, which are given to illustrate and not to limit the invention.

EXAMPLE 1

Preparation of 2-phenyl-indene 20 ml of triethylamine, 2.2 g (20 mmole) of indene, 4.08 g (20 mmole) of iodobenzene and 0.134 g (0.6 mmole) of Pd(OAc)₂ were stirred under reflux for 10 h. After that the mixture was cooled to room temperature and treated with 100 ml of ethanol. The crystalline precipitate was isolated, washed with ethanol and dried under vacuum to obtain 1.6 g (46%) of 2-phenyl-indene.

¹H NMR (CD₂Cl₂): 7.50–7.00 (m, 10H); 3.80 (s, 2H).

EXAMPLE 2

Preparation of 2-(4-nitro-phenyl)-indene 20 ml of triethylamine, 2.2 g (20 mmole) of indene, 4.98 g (20 mmole) of para-nitro iodo-benzene and 0.134 g (0.6 mmole) of Pd(OAc)₂ were stirred under reflux for 10 h. After that the mixture was cooled to room temperature and treated with 100 ml of ethanol. The crystalline yellow precipitate was isolated, recrystallized from ethanol, washed with cold ethanol and dried under vacuum to obtain 1.94 g (41%) of 2-(4-nitro-phenyl)-indene.

¹H NMR (CDCl₃): 8.22 (d, 2H); 7.74 (d, 2H); 7.49 (d, 1H); 7.44 (d, 1H); 7.43 (s, 1H); 7.33–7.23 (m, 2H); 3.82 (s, 2H).

EXAMPLE 3

Preparation of 2-(4-chloro-phenyl)-indene 20 ml of triethylamine, 2.2 g (20 mmole) of indene, 4.77 g (20 mmole) of para-chloro iodo-benzene and 0.134 g (0.6 mmole) of Pd(OAc)₂ were stirred under reflux for 10 h. After that the mixture was cooled to room temperature and treated with 100 ml of ethanol. The crystalline precipitate was isolated, washed with cold ethanol and dried under vacuum to obtain 2.53 g (56%) of 2-(4-chloro-phenyl)-indene.

¹H NMR (CD₂Cl₂): 7.58 (d, 2H); 7.48 (d, 1H); 7.40 (d, 1H); 7.36 (d, 2H); 7.29 (t, 1H); 7.24 (s, 1H); 7.21 (t, 1H); 3.75 (s, 2H).

EXAMPLE 4

Preparation of 2-(4-methoxy-phenyl)-indene 20 ml of triethylamine, 2.2 g (20 mmole) of indene, 4.68 g (20 mmole) of para-methoxy iodo-benzene and 0.134 g (0.6 mmole) of Pd(OAc)₂ were stirred under reflux for 10 h. After that the mixture was cooled to room temperature and treated with 100 ml of ethanol. The crystalline precipitate was isolated, washed with cold ethanol and dried under vacuum to obtain 2.23 g (50%) of 2-(4-methoxy-phenyl)-indene.

¹H NMR (CD₂Cl₂): 7.59 (d, 2H); 7.46 (d, 1H). 7.36 (d, 1H); 7.24 (t, 1H); 7.14 (t, 1H); 7.11 (s, 1H); 6.93 (d, 2H); 3.83 (s, 3H); 3.77 (s, 2H).

EXAMPLE 5

Preparation of 2-(4-carbethoxy-phenyl)-indene 20 ml of triethylamine, 2.2 g (20 mmole) of indene, 5.52 g (20 mmole) of para-carbethoxy iodo-benzene and 0.134 g (0.6 mmole) of Pd(OAc)₂ were stirred under reflux for 10 h. After that the mixture was cooled to room temperature and treated with 100 mnl of ethanol. The crystalline precipitate was isolated, washed with cold ethanol and dried under vacuum to obtain 3.1 g (59%) of 2-(4-carbethoxy-phenyl)-indene.

¹H NMR (CD₂Cl₂): 8.10 (d, 2H); 7.70 (d, 2H); 7.50 (d, 1H); 7.44 (d, 1H); 7.38 (s, 1H); 7.30 (t, 1H); 7.23 (t, 1H); 4.38 (q, 2H); 3.80 (s, 2H); 1.40 (t, 3H).

EXAMPLE 6

Preparation of 2-(3-carboxy-phenyl)-indene 20 ml of triethylamine, 2.2 g (20 mmole) of indene, 4.96 g (20 mmole) of meta-carboxy iodo-benzene and 0.134 g (0.6 mmole) of Pd(OAc)₂ were stirred under reflux for 10 h. After that the mixture was cooled till room temperature and treated with 100 ml of ethanol. The crystalline precipitate was isolated, and dissolved in aqueous alkali. Aqueous phase was separated and treated with aqueous HCl. White precipitated was isolated washed with cooled ethanol and dried under vacuum to obtain 2 g (43%) of 2-(4-carboxy-phenyl)-indene.

¹H NMR (CDCl₃): 8.41 (s, 1H); 8.06 (d, 1H); 7.93 (d, 1H); 7.58–7.25 (m, 6H); 4.7 (br.s); 3.80 (s, 2H).

EXAMPLE 7

Preparation of 2-(3,5-bis-(trifluoromethyl)-phenyl)-indene 20 ml of triethylamine, 2.2 g (20 mmole) of indene, 6.8 g (20 mmole) of 1-iodo-3,5-bis(trifluoromethyl)-benzene and 0.134 g (0.6 mmole) and 0.134 g (0.6 mmole) of Pd(OAc)₂ were stirred under relux for 12 h. After it all triethylamine was removed under reduced pressure. The residue was treated with the mixture 50 ml of water and 50 ml of diethyl ether.

Etherial layer was separated, washed twice with water, filtered and dried over $Na_2SO_4$. Ether was removed and some 20 ml of pentane were added to the reaction mixture, it was cooled down to −20° C. and product was crystallized as dark needle crystals, which were filtered, washed with small portion of cold pentane and dried in vacuum. The yield of product was 32%. $^1$H NMR ($CDCl_3$): 8.06 (bs, 2H); 7.80 (bs, 1H); 7.58–7.48 (m, 3H); 7.42–7.32 (m, 2H); 3.88 (s, 2H).

EXAMPLE 8
Preparation of 2-phenyl-4,7-dimethyl-indene 20 ml of triethylamine, 2.88 g (20 mmole) of 4,7-dimethyl-indene, 4.08 g (20 mmole) of iodobenzene and 0.134 g (0.6 mmole) of $Pd(OAc)_2$ were stirred under reflux for 12 h. After it all the triethylamine was removed under reduced pressure. The residue was treated with the mixture 50 ml of water and 50 ml of diethyl ether. Etherial layer was separated, washed twice with water, filtered and dried over $Na_2SO_4$. Ether was removed and some 20 ml of pentane were added to the reaction mixture. It was cooled down to −20° C. and product was crystallized as white crystals, which were filtered, washed with small portion of cold pentane and dried in vacuum. The yield of product was 38%.

$^1$H NMR ($CDCl_3$): 7.46 (bs, 5H); 7.06 (bs, 2H); 6.48 (t, 1H); 3.45 (d, 2H); 2.47 (s, 3H); 2.08 (s, 3H).

EXAMPLE 9
Preparation of 2-phenyl-benzindene 20 ml of triethylamine, 3.32 g (20 mmole) of benzindene, 4.08 g (20 mmole) of phenyl-iodide and 0.134 g (0.6 mmole) of $Pd(OAc)_2$ were stirred under reflux for 10 h. After that the mixture was cooled to room temperature and treated with 100 ml of ethanol. The crystalline precipitate was isolated, washed with ethanol and dried under vacuum to obtain 2.4 g (50%) of the mixture of two isomers.

$^1$H NMR ($CDCl_3$): 8.2–7.2 (complicated multiplet, 12H); 4.13 (s) and 3.95 (s) total amount 2H.

EXAMPLE 10
Preparation of 2-(4-methoxy-phenyl)-benzindene 20 mnl of triethylamine, 3.32 g (20 mmole) of benzindene, 4.68 g (20 mmole) of p-methoxy-phenyl-iodide and 0.134 g (0.6 mmole) of $Pd(OAc)_2$ were stirred under reflux for 10 h. After that the mixture was cooled to room temperature and treated with 100 ml of ethanol. The crystalline precipitate was isolated, washed with ethanol and dried under vacuum to obtain 2.9 g (54%) of the mixture of two isomers.

$^1$H NMR ($CDCl_3$): 8.2–6.9 (complicated multiplet, 11H); 4.09 (s) and 3.91 (s) total amount 2H; 53.84 (s, 3H).

EXAMPLE 11
Preparation of 2-(4-arbethoxy-phenyl)-benzindene 20 ml of triethylamine, 3.32 g (20 mmole) of benzindene, 5.52 g (20 mmole) of p-carbethoxy-phenyl-iodide and 0.134 g (0.6 mmole) of $Pd(OAc)_2$ were stirred under reflux for 10 h. After that the mixture was cooled to room temperature and treated with 100 ml of ethanol. The crystalline precipitate was isolated, washed with ethanol and dried under vacuum to obtain 3.96 g (63%) of the mixture of two isomers.

$^1$H NMR ($CDCl_3$): 8.2–7.3 (complicated multiplet, 11H); 4.40 (m, 2H); 4.09 (s) and 3.92 (s) total amount 2H; 1.43 (m, 3H).

EXAMPLE 12
Preparation of 2-(4-methoxy-phenyl)-5,6-benzindene 20 ml of triethylamine, 3.32 g (20 mmole) of 5.6-benzindene, 4.68 g (20 mmole) of p-methoxy-phenyl-iodide and 0.134 g (0.6 mmole) of $Pd(OAc)_2$ were stirred under reflux for 10 h. After that the mixture was cooled to room temperature and treated with 100 ml of ethanol. The crystalline precipitate was isolated, washed with ethanol and dried under vacuum to obtain 1.9 g (36%) of the product.

$^1$H NMR (DMSO-$d_6$): 8.2–6.9 (complicated multiplet, 11H); 3.95 (s, 2H). 3.82 (s, 3H).

EXAMPLE 13
Preparation of 2-(1-naphtyl)-indene 20 ml of triethylarine, 2.2 g (20 mmole) of indene, 5.08 g (20 mmole) of 1-naphtyl-iodide and 0.134 g (0.6 mmole) of $Pd(OAc)_2$ were stirred under reflux for 10 h. After that the mixture was cooled to room temperature and evaporated. The residual oil was recrystallized from ethanol and dried under vacuum to obtain 1.5 g (31%) of the product.

$^1$H NMR ($CD_2Cl_2$): 8.2–7.1 (complicated multiplet, 12H); 3.95 (s, 2H).

EXAMPLE 14
Preparation of 4,4'-bis-(2-indenyl)- 1,2-diphenylethane 70 ml of triethylamine, 13.02 g (30 mmole) of 4,4'-diiodo-1,2-diphenylethane, 15.3 ml (120 mmole) of indene and 0.4 g of $Pd(OAc)_2$ were stirred under reflux in nitrogen atmosphere for 16 h. After that the mixture was cooled to room temperature and treated twice with 200 ml of ethanol. The resulting solid was dried under vacuum and the desired product was separated by column chromatography on silica gel using a mixture hexane-dichloromethane (9:1) as an eluent. The chromatography process was controlled by TLC and the 3-d mark was correspondent to this compound. The yield of white crystalline product was 19%.

$^1$H NMR ($CDCl_3$): 7.5–6.8 (m, 18H); 3.74 (s, 4H); 2.82 (s, 4H).

EXAMPLE 15
Preparation of 2-(4-acethyl-phenyl)-indene 20 ml of triethylamine, 2.2 g (20 mmol) of indene, 4.92 g (20 mmol) of para-acethyl-iodo-benzene and 0.134 g (0.6 mmol) of $Pd(OAc)_2$ were stirred under reflux for 10 h. After that all triethylamine was removed under reduced pressure. The residue was treated with the mixture 50 ml of dichloromethane and 50 ml of water. Organic layer was separated, washed twice with water, filtred and dried over $Na_2SO_4$. Dichloromethane was removed and the residue was recrystallized from 20 ml of EtOH. The yield of product was 78%.

$^1$H NMR ($CDCl_3$): 7.95 (d, 2H), 7.68 (d, 2H); 7.48 (d, 1H), 7.43 (d, 1H); 7.35 (s, 1H); 7.29 (t, 1H); 7.21 (t, 1H); 3.80 (s, 2H); 2.60 (s, 3H)

EXAMPLE 16
Preparation of 2-(4-amino-phenyl)-indene 20 ml of triethylamine, 2.2 g (20 mmol) of indene, 4.38 g (20 mmol) of para-amino-iodo-benzene and 0.134 g (0.6 mmol) of $Pd(OAc)_2$ were stirred under reflux for 10 h. After that all triethylamine was removed under reduced pressure. The residue was treated with 80 ml of 15% HCl. Forming precipitate was separated and washed with dichloromethane. The resulting substance was treated with the mixture 50 ml of dichloromethane and 50 ml of 5% KOH in water. Organic layer was separated, washed twice with water, filtered and dried over $Na_2SO_4$. Dichloromethane was removed and the residue was recrystallized from 20 ml of EtOH. The yield of product was 21%.

$^1$H NMR ($CDCl_3$): 7.46 (d, 2H); 7.44 (d, 1H); 7.36 (d, 1H), 7.26 (t, 1H); 7.14 (t, 1H); 7.04 (s, 1H); 6.70 (d, 2H); 3.75 (br.s, 2H); 3.73 (s, 2H)

EXAMPLE 17
Preparation of 2-(4-methyl-phenyl)-indene 20 ml of triethylamine. 2.2 g (20 mmol) of indene, 4.36 g (20 mmol) of para-methyl-iodo-benzene and 0.134 g (0.6 mmol) of Pd(OAc)$_2$ were stirred under reflux for 10 h. After that all triethylamine was removed under reduced pressure. The residue was treated with the mixture 50 ml of dichloromethane and 50 ml of water. Organic layer was separated, washed twice with water, filtered and dried over Na$_2$SO$_4$. Dichloromethane was removed and the residue was recrystallized from 20 ml of EtOH. The yeld of product was 41%.

$^1$H NMR (CDCl$_3$): 7.53 (d, 2H); 7.46 (d, 1H), 7.38 (d, 1H), 7.27 (t, 1H); 7.19 (d, 2H); 7.18 (s, 1H); 7.17 (t, 1H); 3.77 (s, 2H); 2.37 (s, 3H)

EXAMPLE 18
Preparation of 2-(4-acetamido-phenyl)-indene 20 ml of triethylamine, 2.2 g (20 mmol) of indene, 5.22 , (20 mmol) of para-acetamino-iodo-benzene and 0.134 g (0.6 mmol) of Pd(OAc)$_2$ were stirred under reflux for 10 h. After that all triethylamine was removed under reduced pressure. The residue was treated with the mixture 50 ml of dichloromethane and 50 ml of water. Organic layer was separated, washed twice with water, filtered and dried over Na$_2$SO$_4$. Dichloromethane was removed and the residue was recrystallized from 20 ml of EtOH. The yeld of product was 13%.

$^1$H NMR (CDCl$_3$): 7.59 (d, 2H); 7.52 (d, 2H); 7.46 (d, 1H), 7.38 (d, 1H); 7.26 (t, 1H); 7.18 (t, 1H); 7.17 (s, 1H); 3.77 (s, 2H); 2.20 (s, 3H)

EXAMPLE 19
Preparation of 2,5-diphenyl-4-aza-indene (as 1:1 mixture with its isomer)

20 ml of triethylamine, 3.86 g (20 mmol) of 5-phenyl-4-aza-indene, 4.08 g (20 mmol) of iodo-benzene and 0.134 g (0.6 mmol) of Pd(OAc)$_2$ were stirred under reflux for 10 h. After that all triethylamine was removed under reduced pressure. The residue was treated with the mixture 50 ml of dichloromethane and 50 ml of water. Organic layer was separated, washed twice with water, filtered and dried over Na$_2$SO$_4$. Dichloromethane was removed and the residue was recrystallized from 20 ml of EtOH. The yeld of product was 23%.

$^1$H NMR (CDCl$_3$): 8.1–7.2 (multiplet, 13H); 3.97 (d) and 3.83 (dd), totally 2H.

EXAMPLE 20
Preparation of 4-acetoanylyde-phenyl-indene 20 ml of DMF, 2,9 ml (25 mmol) of indene, 6,4 g (25 mmol) of para-acetoacetoamino-iodo-benzene, 3 ml of triethylamine and 0.18 (0.75 mmol) of Pd(OAc)$_2$ were stirred under reflux for 10 hours. The resulting mixture was poured into 100 ml water. The forming precipitate was isolated, washed with 10 ml cold chloroform and dried. The yeld of product was 75%.

EXAMPLE 21
Preparation of 4-amino-phenyl-indene 20 ml of DMF, 2.2 g (20 mmol) of indene, 4,4 g (20 mmol) of para-amino-iodo-benzene, 2 ml of triethylamine and 0,134 (0,6 mmol) of Pd(OAc)$_2$ were stirred under reflux for 10 h. The resulting mixture was poured into 200 ml of 15% HCl. Forming precipitate was separated and washed with dichloromethane. The resulting substance was treated with the mixture 50 ml of dichloromethane and 50 ml of 5% KOH in water. Organic layer was separated, washed twice with water, filtered and dried over Na$_2$SO$_4$. Dichloromethane was removed and the residue was recrystallized from 20 ml of EtOH. The yeld of product was 70%.

EXAMPLE 22
Preparation of 4-nitro-phenyl-indene 15 ml of DMF, 1,15 g (10 mmol) of indene, 2,49 g (10 mmol) of para-nitro-iodo-benzene, 1 ml of triethylamine and 0,067 (0,3 mmol) of Pd(OAc)$_2$ were stirred under reflux for 10 h. The resulting mixture was poured into the mixture of 50 ml of dicloromethane and 50 ml of water. Organic layer was separated, washed twice with water, filtered and dried over Na$_2$SO$_4$. Dicloromethane was removed and the residue was recrystallized from 20 ml of EtOH. The yeld of product was 16%.

EXAMPLE 23
Preparation of 2-(4-biphenylo)-indene 20 ml of DMF, 2,2 g (20 mmol) of indene, 5,60 g (20 mmol) of 4-iodo-biphenyl, 2 ml of triethylamine and 0,134 (0,6 mmol) of Pd(OAc)$_2$ were stirred under reflux for 10 h. The resulting mixture was poured into the mixture of 250 ml of dicloromethane and 50 ml of water. Organic layer was separated, washed twice with water, filtered and dried over Na$_2$SO$_4$. Dicloromethane was removed and the residue was recrystallized from 20 ml of DMF. The yeld of product was 21%.

$^1$H NMR (CDCl$_3$): 7.8–7.1 (multiplet, 14H); 3.81 (s, 2H)

EXAMPLE 24
Preparation of 2-phenyl-indene 20 ml of DMF, 2.2 g (20 mmol) of indene, 2.2 ml (20 mmol) of iodo-benzene, 2 ml of triethylamine and 0,134 (0,6 mmol) of Pd(OAc)$_2$ were stirred under reflux for 10 hours. The resulting mixture was poured into the mixture of 50 ml of dicloromethane and 50 ml of water. Organic layer was separated, washed twice with water, filtered and dried over Na$_2$SO$_4$. Dicloromethane was removed and the residue was recrystallized from 20 ml of EtOH. The yeld of product was 65%.

What is claimed is:

1. A process for the preparation of 2-aryl-substituted indenes of the formula (I):

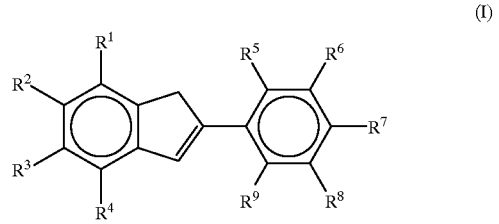

wherein:
R$^1$, R$^2$, R$^3$, R$^4$, R$^5$, R$^6$, R$^7$, R$^8$ and R$^9$, same or different, are hydrogen atoms, halogen atoms, C$_1$–C$_{20}$) alkyl, C$_3$–C$_{20}$) cycloalkyl. C$_2$–C$_{20}$) alkenyl, C$_6$–C$_{20}$aryl, C$_7$–C$_{20}$ alkylaryl, C$_7$–C$_{20}$ arylalkyl, NO$_2$, NR$^{10}$$_2$, OH, OR$^{11}$, COOH, COOR$^{12}$, COH or COR$^{13}$ groups, optionally containing Si or Ge atoms, any two adjacent R$^1$, R$^2$, R$^3$, R$^4$, R$^5$, R$^6$, R$^7$, R$^8$ and R$^9$ substituents optionally forming an aromatic or aliphatic ring comprising from 5 to 8 carbon atoms, and one of R$^1$, R$^2$, R$^3$, R$^4$, R$^5$, R$^6$, R$^7$, R$^8$ and R$^9$ being optionally linked with a corresponding R$^1$, R$^2$, R$^3$, R$^4$, R$^5$, R$^6$, R$^7$, R$^8$ and R$^9$ of a second indene compound of the formula (I) to form a structural bridging group, R$^{10}$, R$^{11}$, R$^{12}$ and R$^{13}$ being C$_1$–C$_{20}$ alkyl, C$_3$–C$_{20}$ cycloalkyl, C$_2$–C$_{20}$ alkenyl, C$_6$–C$_{20}$ aryl, C$_7$–C$_{20}$ alkylaryl or $C_7$–$C_{20}$ arylalkyl radicals, optionally an aromatic carbon atom of the indene ring being replaced by a hetero atom selected from those belonging to group 15 of the Periodic Table of the Elements (new IUPAC version), the $R^1$, $R^2$, $R^3$ or $R^5$ substituent on the replaced carbon atom being absent, said process comprising the reaction of an indene of the formula (II):

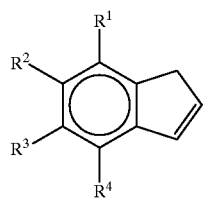

(II)

wherein $R^1$, $R^2$, $R^3$ and $R^4$ have the meaning given above, one of $R^1$, $R^2$, $R^3$ and $R^4$ being optionally linked with a corresponding $R^1$, $R^2$, $R^3$ and $R^4$ of a second indene of the formula (II) to form a structural bridging group, optionally an aromatic carbon atom of the indene ring being replaced by a hetero atom selected from those belonging to group 15 of the Periodic Table of the Elements (new IUPAC version), the $R^1$, $R^2$, $R^3$ or $R^4$ substituent on the replaced carbon atom being absent, with an arene compound of the formula (III):

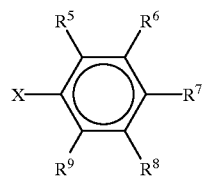

(III)

wherein X is an halogen atom, preferably a iodine atom, or an organosulphonate group, $R^5$, $R^6$, $R^7$, $R^8$ and $R^9$ have the meaning given above, one of $R^5$, $R^6$, $R^7$, $R^8$ and $R^9$ being optionally linked with a corresponding $R^5$, $R^6$, $R^7$, $R^8$ and $R^9$ of a second arene compound of the formula (III) to form a structural bridging group, said reaction being carried out in a basic medium in the presence of a palladium catalyst.

2. The process according to claim 1, wherein the reaction is carried out in the presence of a base which acts as a solvent.

3. The process according to claim 2, wherein the base is a primary, secondary or tertiary amine.

4. The process according to claim 3, wherein the base is triethylamine.

5. The process according to claim 1, wherein the reaction is carried out in a mixture containing a polar solvent and a tertiary amine.

6. The process according to claim 5, wherein the polar solvent is N,N-dimethylformamide (DMF) and the tertiary amine is triethyl amine.

7. The process according to claim 5, wherein the volume ratio of the polar solvent to the tertiary amine is in the range between 1:100 and 100:1.

8. The process according to claim 1, wherein the palladium catalyst is selected from palladium(0) and palladium (II) compounds.

9. The process according to claim 8, wherein the palladium catalyst is palladium acetate.

10. The process according to claim 1, wherein in the arene compound of the formula (III), X is a iodine atom.

11. The process according claim 1, wherein in the arene compound of the formula (III), the $R^5$ and $R^9$ substituents are hydrogen atoms.

12. The process according to claim 1, wherein the indene of the formula (II) and the arene compound of the formula (III) are used in substantially equimolar amounts.

13. A 2-aryl-substituted indene of the formula (I):

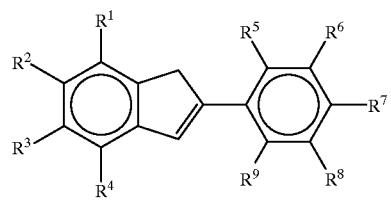

(I)

wherein $R^1$, $R^2$, $R^3$, $R^4$, $R^5$, $R^6$, $R^7$, $R^8$ and $R^9$, same or different, have the meaning recited in claim 1, one of $R^1$, $R^2$, $R^3$, $R^4$, $R^5$, $R^6$, $R^7$, $R^8$ and $R^9$ and the corresponding $R^1$, $R^2$, $R^3$, $R^4$, $R^5$, $R^6$, $R^7$, $R^8$ and $R^9$, of a second indene compound of the formula (I) being replaced by a structural bridging group linking the two indenes.

14. The 2-aryl-substituted indene according to claim 13, wherein the structural bridge is an alkylene group.

15. The 2-aryl-substituted indene according to claim 13, which is selected from the group consisting of:

4,4'-bis-(2-indenyl)-1,2-diphenylethane, and
1,2-bis(2-phenyl-4-indenyl)ethane.

16. A 2-aryl-substituted indene of the formula (I):

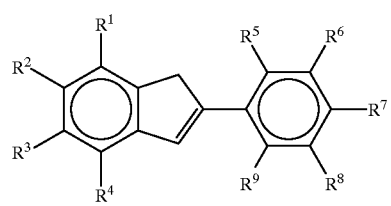

(I)

wherein $R^1$, $R^2$, $R^3$, $R^4$, $R^5$, $R^6$, $R^7$, $R^8$ and $R^9$, same or different, have the meaning as recited in claim 1, except that $R^1$ and $R^4$ cannot be COOH, wherein an aromatic carbon atom of the indene ring is replaced by a hetero atom selected from those belonging to group 15 of the Periodic Table of the Elements (new IUPAC version), the $R^1$, $R^2$, $R^3$ or $R^4$ substituent on the replaced carbon atom being absent.

* * * * *